United States Patent
Hossack et al.

(10) Patent No.: US 6,712,767 B2
(45) Date of Patent: Mar. 30, 2004

(54) ULTRASONIC IMAGING DEVICES AND METHODS OF FABRICATION

(75) Inventors: Norman Hugh Hossack, Folsom, CA (US); Andrew Thomas Jeffrey, Rangendingen (DE); Elvin Leonard Nix, London (GB)

(73) Assignee: Volcano Therapeutics, Inc., Laguna Hills, CA (US)

( * ) Notice: Subject to any disclaimer, the term of this patent is extended or adjusted under 35 U.S.C. 154(b) by 0 days.

(21) Appl. No.: 10/233,893

(22) Filed: Aug. 29, 2002

(65) Prior Publication Data

US 2004/0044286 A1 Mar. 4, 2004

(51) Int. Cl.⁷ ................................................ A61B 8/12
(52) U.S. Cl. ................................... 600/467; 604/102.2
(58) Field of Search ........................... 600/462–463, 600/466–467, 471; 604/96.01, 97.01, 102.1–102.2; 264/234, 342 R; 156/242, 300

(56) References Cited

U.S. PATENT DOCUMENTS

| 4,665,925 A | * | 5/1987 | Millar ........................ 600/585 |
| 4,762,129 A | | 8/1988 | Bonzel |
| 4,911,170 A | * | 3/1990 | Thomas et al. ............. 600/463 |
| 4,917,097 A | | 4/1990 | Proudian et al. |
| 5,167,233 A | | 12/1992 | Eberle et al. |
| 5,174,295 A | * | 12/1992 | Christian et al. ........... 600/468 |
| 5,660,180 A | * | 8/1997 | Malinowski et al. ....... 600/439 |
| 5,779,644 A | | 7/1998 | Eberle et al. |
| 5,857,974 A | | 1/1999 | Eberle et al. |
| 5,876,344 A | | 3/1999 | Baker et al. |
| 5,947,905 A | | 9/1999 | Hadjicostis et al. |
| 6,049,958 A | | 4/2000 | Eberle et al. |
| 6,080,109 A | * | 6/2000 | Baker et al. ................. 600/463 |
| 6,238,347 B1 | | 5/2001 | Nix et al. |
| 6,283,921 B1 | | 9/2001 | Nix et al. |

FOREIGN PATENT DOCUMENTS

WO  WO 02/07601  1/2002

* cited by examiner

*Primary Examiner*—Francis J. Jaworski
(74) *Attorney, Agent, or Firm*—Nicola A. Pisano; Luce, Forward, Hamilton & Scripps (57) ABSTRACT

An ultrasound catheter suitable for insertion in the body lumens of a patient during medical procedures is provided. An ultrasound transducer may be provided at the distal tip of the catheter. An inflatable balloon may be provided at the distal end of the catheter on the proximal side of the ultrasound transducer. The catheter may have lumens for inflation fluid, electrical wires, and a guide wire. A sheath that runs through the balloon may be used to isolate the electrical wires and guide wire from inflation fluid in the interior of the balloon.

22 Claims, 9 Drawing Sheets

ULTRASONIC IMAGING DEVICES AND METHODS OF FABRICATION

BACKGROUND OF THE INVENTION

This application relates to ultrasonic imaging devices such as ultrasonic imaging catheters and to methods for fabricating these devices.

Ultrasonic imaging techniques are often used to gather images during medical procedures. For example, ultrasonic imaging catheters may be used to gather images from within the body lumens of a patient during the diagnosis and treatment of medical conditions. During percutaneous transluminal coronary angioplasty procedures, images may be acquired from within the blood vessels of a cardiac patient to help a physician to accurately place an expandable balloon.

In a typical ultrasound imaging catheter configuration, a piezoelectric ultrasound transducer array near the distal end of the catheter may be used to generate high-frequency acoustic signals that radiate towards the image target (e.g., a patient's blood vessel). The transducer array also gathers corresponding reflected acoustic signals. Image processing techniques are used to convert the reflected acoustic signals into images for the physician.

When the expandable balloon and ultrasound transducer are part of the same catheter, size and placement considerations have generally dictated that the ultrasound transducer be located at a more proximal location than the balloon. With this arrangement, the ultrasound transducer is offset from the distal tip of the catheter by at least the length of the balloon. The images from the ultrasound transducer therefore cover a portion of the patient's blood vessel that is offset from the distal tip of the catheter being advanced into the patient's blood vessel by the physician. It would be desirable to reduce or eliminate this offset to improve the physician's view of the patient's blood vessel in the vicinity of the distal catheter tip. Also, in many cases it is desirable to cross a lesion with an imaging device prior to crossing the lesion with a therapeutic device so that the treatment site may be visualized prior to crossing.

It is an object of the present invention to provide ultrasonic imaging catheters in which the ultrasound transducer is located distally and an expandable balloon is located proximally on the distal end of the catheter.

It is also an object of the present invention to provide ultrasonic imaging catheters with distally-located ultrasound transducers having small crossing profiles.

It is another object of the present invention to provide improved techniques for fabricating ultrasound imaging catheters.

SUMMARY OF THE INVENTION

These and other objects of the invention are accomplished in accordance with the principles of the invention by providing ultrasonic imaging catheters with ultrasound transducers at their tips and by providing modular and non-modular methods for fabricating these catheters.

An imaging catheter constructed in accordance with the invention may have an ultrasound sensor at its distal tip. The imaging catheter may be used in an ultrasound imaging system to gather ultrasound images for a physician or other user.

The sensor may have a transducer array formed from piezoelectric elements. The piezoelectric elements may be mounted on a flexible substrate. The flexible substrate may include conductive lines and integrated circuits for handling the signals conveyed to and from each of the transducer array elements. The flexible substrate and mounted components may be referred to as a "flex circuit." The flex circuit may be wrapped around a guide wire lumen to form an ultrasound transducer assembly with an integral guide wire lumen.

The ultrasound transducer assembly may be attached to the distal tip of the catheter. This transducer location provides good diagnostic imaging capabilities for the user of the ultrasound imaging system. An expandable balloon (e.g., a balloon suitable for expanding a patient's blood vessels during angioplasty or for deploying a stent) may be located on the proximal side of the ultrasound transducer. This allows the imaging catheter to be used as a treatment device.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
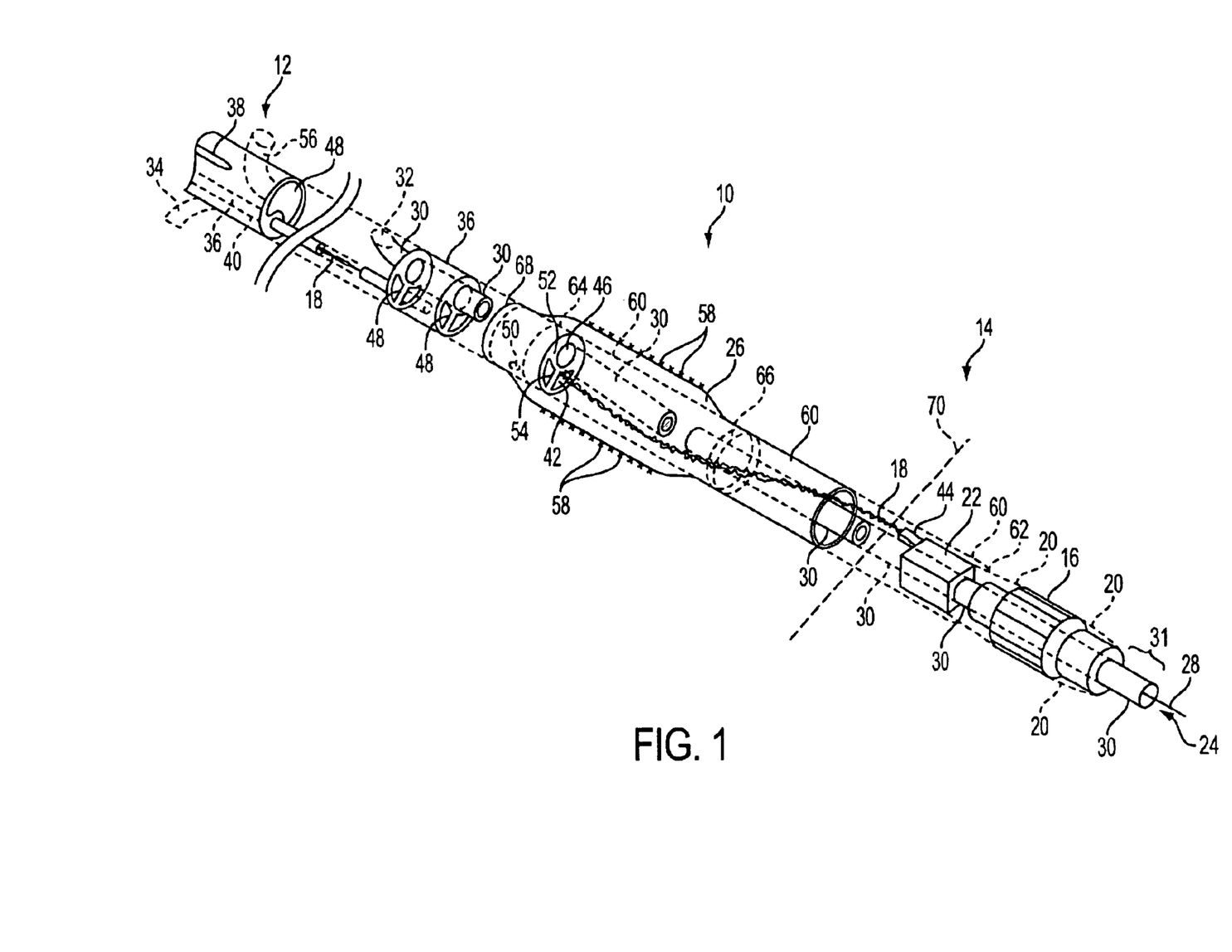
FIG. 1 is a perspective view of an illustrative ultrasonic imaging catheter with a balloon in accordance with the present invention.

An illustrative catheter-based ultrasonic imaging system in accordance with the invention may have an imaging catheter 10 as shown in FIG. 1. Catheter 10 may be connected to external imaging equipment that performs digital image processing functions and that displays ultrasound images from catheter 10 to a physician or other user. The catheter and imaging equipment allow the user to position the catheter properly during diagnostic and treatment procedures.

As shown in FIG. 1, catheter 10 has a proximal end 12 that is connected to the imaging equipment and a distal end 14 that may be inserted into a patient (e.g., in a blood vessel during an angioplasty procedure). The catheter 10 has an ultrasound transducer 16. An electrical cable 18 is used to electrically connect the ultrasound transducer 16 to the imaging equipment. The ultrasound transducer 16 may be formed from a number of piezoelectric transducer elements formed on a flexible substrate ("flex circuit") having integrated conductors that is wrapped in a cylinder around a core ultrasound support structure.

The outline of the flex circuit is shown by dotted line 20 in FIG. 1. Multiplexer integrated circuits 22 and transducer 16 may be mounted on the inner side of flex circuit 20. The flex circuit transducer assembly is preferably located at the distal tip 24 of catheter 10, because this provides the physician with a good view of the images of the patient's blood vessel (or other suitable image target) from an advantageous forward position on the catheter. The catheter 10 may have a balloon 26 that is located on the proximal side of the ultrasound transducer 16.

The components of FIG. 1 are not shown to scale. In a typical catheter, the catheter may be over a meter in length and may have a diameter of about three French (about 1 mm). The distal portion of the catheter in which the balloon 26 and ultrasound transducer 16 reside may, for example, be less than or equal to about 250 mm in length.

The catheter 10 may be guided over a guide wire during use. A portion of a typical guide wire 28 is shown protruding from the distal tip 24 of catheter 10 in FIG. 1. (The rest of the guide wire 28 is not shown in FIG. 1 to avoid overcomplicating the drawing). A guide wire lumen 30 (made up of one or more individual guide wire lumen sections joined together in series) runs axially through at least the distal end of catheter 10.

Catheter 10 may be implemented as either a "rapid exchange" (RX) catheter or as an "over-the-wire" (OTW) catheter. In the "rapid exchange" configuration, the guide wire lumen 30 exits the main catheter shaft at an exit port such as exit port 32. Exit port 32 may be located adjacent or proximal to the proximal end of balloon 26. With the rapid exchange catheter, only the relatively short portion of the catheter from port 32 to tip 24 is guided over the guide wire 28. This allows the overall length of guide wire lumen 30 and guide wire lumen 28 to be substantially reduced and reduces internal friction between the walls of the guide wire lumen and the guide wire.

With an over-the-wire configuration, port 32 may be replaced with a port, such as guide wire exit port 34 that is at the proximal end 12 of the catheter 10. The over-the-wire configuration requires that a longer guide wire be used than in the rapid exchange configuration.

The proximal end 12 of catheter 10 may be formed of a catheter shaft 36, which may be made of plastic or any other suitable flexible material. A stiffening member 38, such as a stainless steel wire, may optionally be used to help stiffen the proximal portion of the catheter. In an over-the-wire configuration, the guide wire lumen may continue within the proximal region of shaft 36 (not shown) and communicate with port 34.

Shaft 36 preferably contains a lumen 40 for housing cable 18. Lumen 40 may be an extruded tubular cavity in the plastic (or other material) of shaft 36 or may be formed using a stainless-steel tube (e.g., hypotube). When provided in a rapid exchange configuration, using hypotube for lumen 40 may help to stiffen catheter 10 at exit port 32, where the guide wire lumen proximally exits the catheter.

Wires 18 may be housed in lumen 40 from the proximal end of catheter 10 until exit port 42 in the distal catheter shaft end face 52. Wires 18 exiting port 42 may be passed along the center of catheter 10 until they reach tab 44 of the flex circuit, where these wires are electrically connected to the transducer circuitry.

Adjacent to cable exit port 42, shaft 36 has a guide wire shaft opening 46 in which the guide wire lumen 30 is placed. During the manufacturing process, the guide wire lumen 30 may be inserted into the opening 46 at the end of shaft 36 and may be pushed or pulled back through the shaft 36 until guide wire lumen 30 exits shaft 36 at port 32 or, alternatively, at port 34. Guide wire lumen 30 is preferably trimmed flush with the surface of catheter 10 to facilitate movement of catheter 10 through a patient's blood vessels or other body lumens during use of the catheter. If desired, guide wire lumen 30 may alternatively be inserted only part way within guide wire shaft opening 46, in which case shaft 36 may form a portion of the guide wire lumen.

Balloon 26 may be inflated by filling the interior of balloon 26 with an inflation fluid (e.g., a sterile saline solution that would not harm the patient in the event that some of the fluid were to leak into the patient's blood vessel). An inflation lumen 48 may be used to introduce the inflation fluid into the interior of balloon 26. Inflation lumen 48 may be connected to the interior of balloon 26 using side port 50.

If the initial bore from which lumen 48 is constructed continues all the way to the exposed end face 52 of shaft 36, it may be filled with a plug 54, so that inflation fluid only flows out through side port 50. If desired, this bore may be directed through the side of shaft 36 to form side port 50 without forming a distal hole that needs to be plugged. Other suitable arrangements may be used if desired. This is merely one illustrative way in which inflation fluid may be introduced into the interior of balloon 26.

An inflation port 56 that communicates with inflation lumen 48 may be provided in the proximal end 12 of catheter 10. The inflation port 56 may be connected to a source of inflation fluid (e.g., a squeezable bulb or computer-controlled reservoir) that is controlled by the user.

When the user forces fluid into port 56, the fluid travels through lumen 48, out side port 50 and into the interior of balloon 26, thereby inflating balloon 26. Balloon 26 may be used by itself or may be provided with a surrounding stent, for example, a drug eluting stent, to be deployed upon inflation of the balloon. Crosses 58 in FIG. 1 illustrate the presence of this optional stent.

A sheath 60 may be used to isolate the electronic components of the transducer and other catheter components such as wires 18 and guide wire lumen 30 from exposure to the inflation fluid in the interior of balloon 26. Sheath 60 may also serve to isolate the electronic components of the transducer and other catheter components from exposure to the blood or other body fluids of the patient.

At its most distal end 62, sheath 60 may be affixed (e.g., using an adhesive or heat weld) to the exterior of flex circuit 20. At its most proximal end 64, the sheath 60 may be attached to the distal end of shaft 36 (e.g., using an adhesive or heat weld), preferably distal of inflation side port 50.

Sheath 60 may be formed of any suitable material such as flexible plastic. If desired, sheath 60 may be formed from a heat-shrinkable material, because heat shrinking sheath 60 over wires 18 and lumen 30 may reduce the exterior dimensions (e.g., the circumference) of catheter 10. The sheath may also be formed from a material that is not heat-shrinkable (e.g., sheath 60 may be formed from a nonshrinkable plastic tubing or other nonshrinkable materials).

Balloon 26 may be distally affixed (e.g., using adhesive or heat welding) to the exterior of sheath 60 (e.g., at distal attachment band or ring 66) and may be proximally affixed to the exterior of catheter shaft 36 (e.g., at proximal attachment band or ring 68). This forms a fluid seal so that fluid in the interior of balloon 26 is contained in a cavity formed between the exterior of sheath 60 and the interior of the balloon 26. Balloon 26 may be formed from an expandable or non-expandable polymer or any other suitable material.

When sheath 60 and balloon 26 have been properly affixed to the exterior of catheter 10, the catheter is sealed so that blood (and other body fluids) cannot penetrate into the interior portions of the catheter. At the proximal end 12 of catheter 36, the exterior of shaft 36 is exposed to the patient's blood. In the vicinity of balloon 26, the exterior of balloon 26 is exposed to the patient's blood. Inflation fluid fills the cavity between the interior of balloon 26 and the exterior of the proximal portion of sheath 60. The distal end of sheath 60 that is connected to the flex circuit may be exposed to the patient's blood.

As shown in FIG. 1, a relatively short length 31 (e.g., 5–10 mm) of the guide wire lumen 30 may protrude from the distal end of the transducer assembly. This tip may be soft, so as to form an a traumatic tip and not to harm the patient's blood vessels as the catheter 10 is advanced into the patient over guide wire 28.

The catheter configuration of FIG. 1 may be used with different types of ultrasound transducer assemblies. In one suitable arrangement, a flex circuit may be wrapped around a support lumen to form a cylindrical transducer. The support lumen may be, for example, a hollow plastic cylinder with integral retainer-ring protrusions or with separate retainer rings configured to abut the ends of the cylindrical transducer. These are, however, merely illustrative arrangements. Any suitable ultrasound transducer arrangements may be used if desired.

The catheter may be fabricated by assembling the components of the transducer and catheter to form the final product. If desired, the transducer portion of the catheter may be manufactured as a separate module that is attached at a final stage to the rest of the catheter assembly (referred to as a "delivery module"). If this type of modular assembly approach is used, the ultrasound transducer and the rest of the catheter may, for example, be divided (before final assembly) along the dotted line 70 shown in FIG. 1. The transducer module may or may not also have a substantial associated length of guide wire lumen 30.

Figure 2:
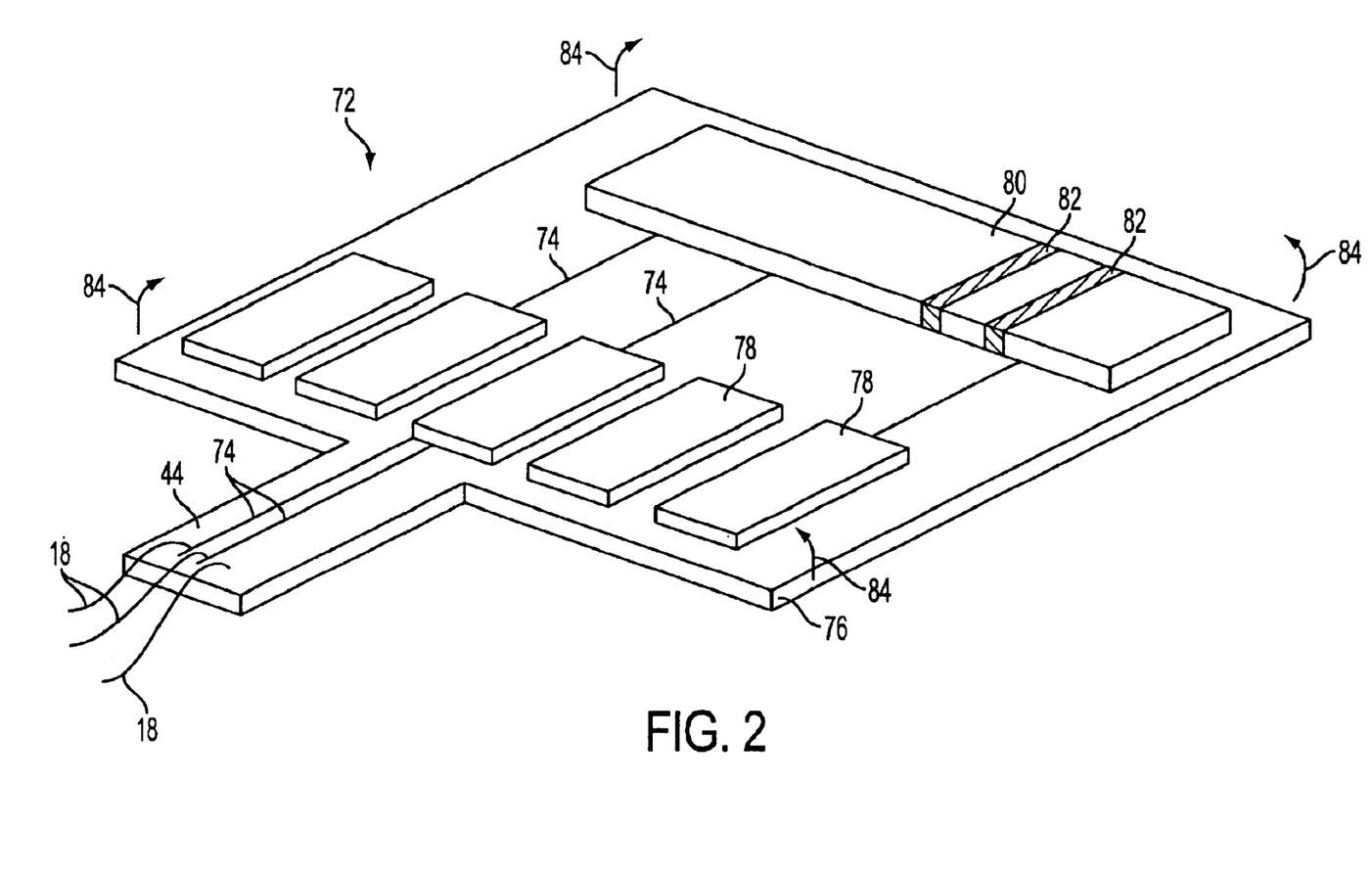
FIG. 2 is a perspective view of an illustrative flex circuit that may be used in forming the ultrasound transducer for the ultrasonic imaging catheter device in accordance with the present invention.

An illustrative flex circuit 72 that may be used for the ultrasound transducer is shown in FIG. 2. As shown in FIG. 2, wires 18 may be attached to conductors 74 on tab portion 44 of flex circuit substrate 76. Conductors 74 may be any suitable conductive lines or traces that have been formed on the surface of substrate 76. Only a few conductors 74 are shown in FIG. 2 to avoid over-complicating the drawing.

The substrate 76 may be formed from a flexible material such as polyimide or other suitable insulator. A transducer array 80 that is formed from a number of individually-controllable transducer elements 82 may be mounted on the end of flex circuit 72. Cable 18 may only contain a few individual wires, whereas there may be 50 or more individual transducer elements 82. Accordingly, multiplexer integrated circuits 78 (multiplexers) may be used to form an interface between the conductors in cable 18 and the transducer elements 82. There are five multiplexers shown in FIG. 2. This is merely illustrative. There may be, for example, four multiplexers. When the flex circuit 72 is wrapped around a suitable support lumen, the multiplexers may form a block-shaped structure of the type shown as multiplexers 22 of FIG. 1.

There are preferably spaces, kerfs, cuts and/or slits between adjacent transducer array elements 82, so that transducer array 80 is not rigid. This allows flex circuit 72 to be curled (as indicated by curved arrows 84) to form a cylinder that is coaxial with the longitudinal axis of a suitable support. Additionally, transducer array elements 82 may each have an acoustic matching layer. Matching layers, kerfs, cuts and slits are described, for example, in Stephens U.S. patent application Ser. No. 10/233,870, filed concurrently herewith, entitled "Ultrasound Imaging Devices and Methods of Fabrication," which is hereby incorporated by reference herein in its entirety.

Figure 3A:
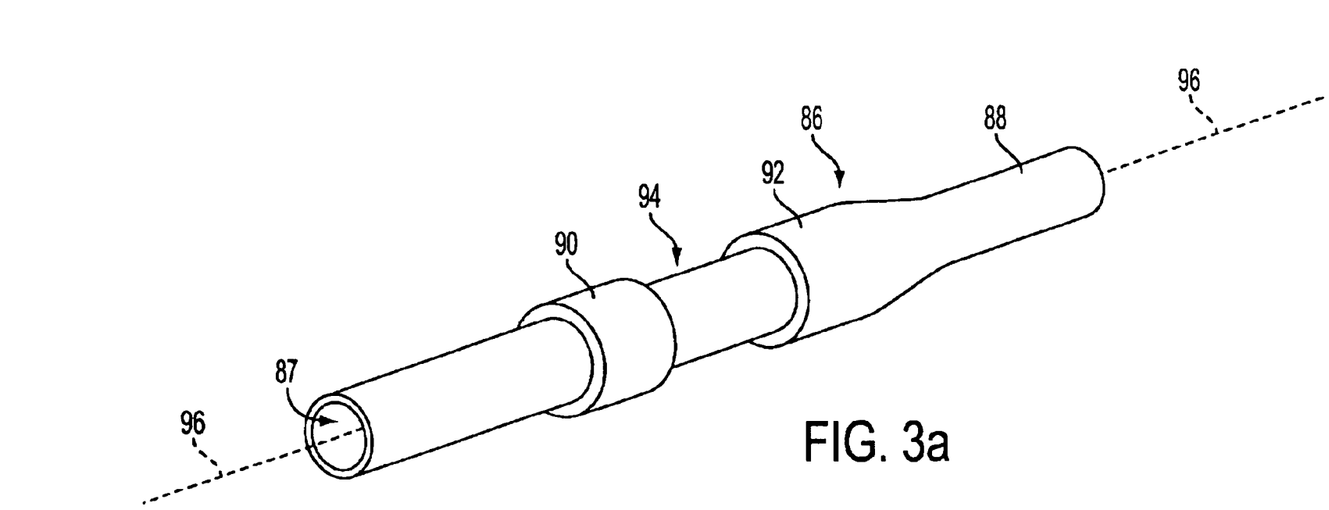
FIG. 3a is a perspective view of an illustrative molded plastic lumen that may be used to support the flex circuit of FIG. 2 in accordance with the present invention.
Figure 3B:
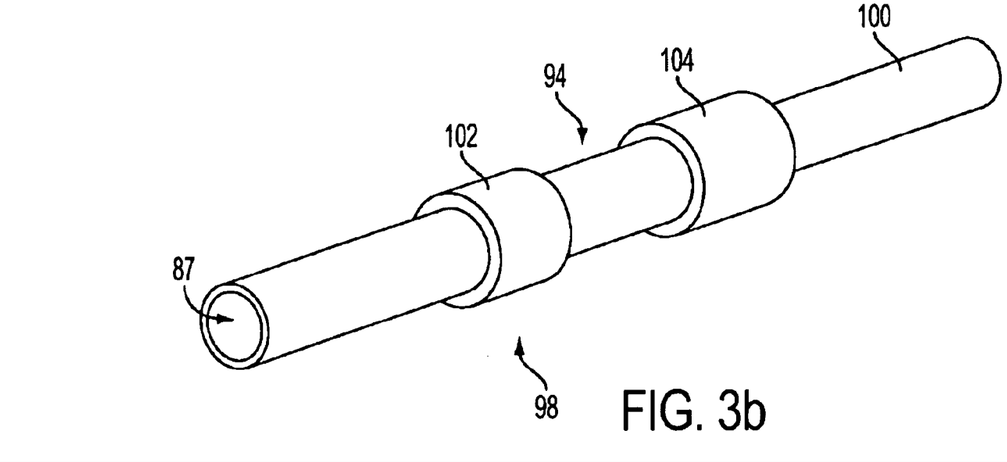
FIG. 3b is a perspective view of an illustrative lumen with retaining rings that may be used to support the flex circuit of FIG. 2 in accordance with the present invention.

Illustrative support structures that may be used to form the core of the transducer assembly are shown in FIGS. 3a and 3b. The illustrative support structure 86 that is shown in FIG. 3a may be formed using a plastic molding process or any other suitable technique. Structure 86 may have a bore 87 that extends alone the longitudinal axis 96 of structure 86 and may serve as a portion of guide wire lumen 30 when the catheter is fully assembled. Tip 88 of structure 86 may form all or part of the portion of guide wire lumen portion 31 shown in FIG. 1 that protrudes towards distal tip 24 at distal end 14 of catheter 10. Retaining ring portions 90 and 92 may be formed as an integral portion of the plastic (or other material) that makes up structure 86. Retaining ring portions 90 and 92 define an annular gap 94 into which transducer array 80 fits when flex circuit is wrapped around structure 86 and longitudinal axis 96.

Another suitable structure for forming the core of the ultrasound transducer portion of the catheter is shown in FIG. 3b. In the example of FIG. 3b, the structure 98 has a hollow tube 100 with a bore 87. The hollow tube 100 may be used to form a distal portion of guide wire lumen 30 (FIG. 1) when the catheter is fully assembled. Separate retaining rings (e.g., ruby retaining rings that have been individually machined and attached to the surface of tube 100) may be positioned along tube 100 to form annular transducer array gap 94.

Figure 4:
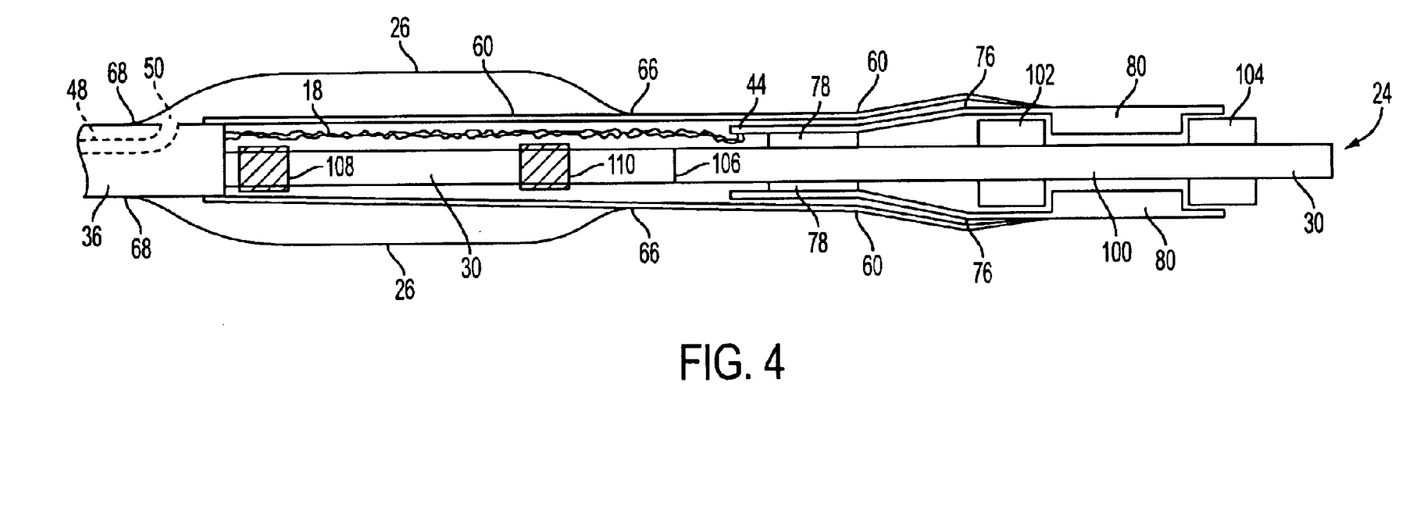
FIG. 4 is a cross-sectional side view of the distal end of an illustrative imaging catheter using an ultrasound transducer support lumen with retaining rings of the type shown in FIG. 3b in accordance with the present invention.

A cross-sectional view of an illustrative ultrasound transducer and some of the surrounding catheter components is shown in FIG. 4. In the example used for the cross-section of FIG. 4, the cylindrical support lumen at the center of the transducer assembly is formed from a support of the type shown in FIG. 3b. Balloon 26 is attached to shaft 36 (at attachment ring region 68) and is attached to the outer portion of sheath 60 (at attachment ring region 66).

The flex circuit substrate 76 is wrapped around support tube 100. The line 106 marks an illustrative location at which tube 100 may be attached to the rest of the tubing that forms guide wire lumen 30. This is merely an illustrative location. If desired tube 100 may be connected to suitable guide wire tubing at another suitable location in catheter 10 or tube 100 may be a single longer piece that forms the entire guide wire lumen 30 by itself.

As shown in FIG. 4, radiopaque markers 108 and 110 (e.g., gold, platinum, or iridium rings) may be attached to the guide wire lumen 30 or other suitable catheter structure to help the physician or other user of catheter 10 position catheter 10 properly under a fluoroscope. One suitable location for these radiopaque markers is at the distal and proximal ends of balloon 26, as shown in FIG. 4. This provides the user with an accurate indication of the position of balloon 26 on a fluoroscope display or an x-ray film.

The ultrasound transducer flex circuit 72 (FIG. 2) may be formed into a cylinder by curling the opposing edges of substrate 76 towards each other, as indicated by arrows 84 in FIG. 2. Such manufacturing techniques are described, for example, in U.S. Pat. No. 6,049,958 to Eberle et al., which is hereby incorporated by reference herein in its entirety. Another suitable approach for wrapping flex circuit 72 around a cylindrical support structure is shown in FIG. 5.

Figure 5:
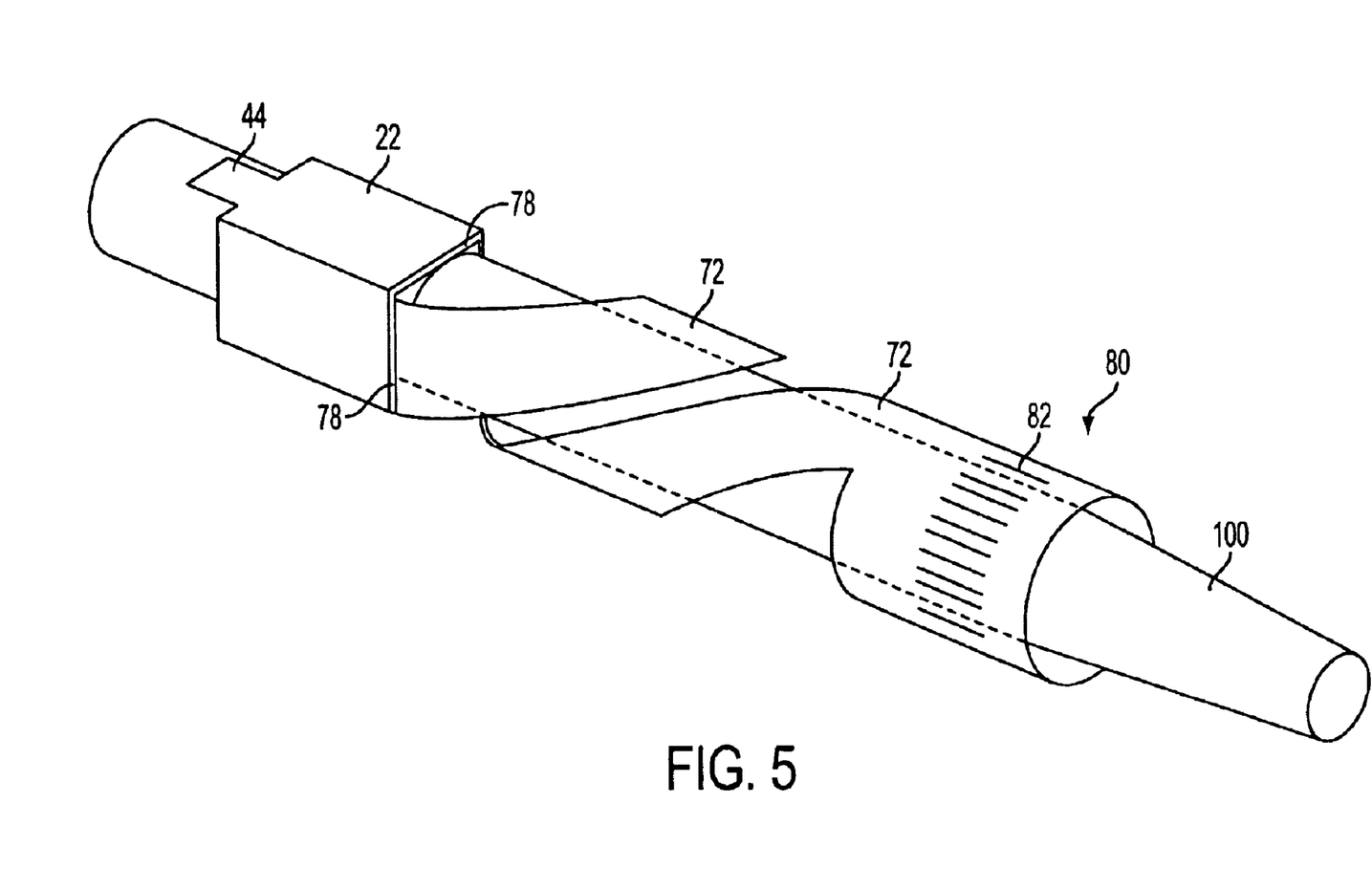
FIG. 5 is a perspective view of an illustrative ultrasound transducer arrangement using a flex circuit that is helically wrapped around a guide wire support lumen in accordance with the present invention.

With the approach of FIG. 5, the flex circuit 72 is cut in a shape that allows it to be wrapped in a helix about support 100. This arrangement may be more compact (i.e., it may have a smaller diameter) than when the flex circuit is curled edge-to-edge and/or may allow independent articulation of integrated circuits 22 and ultrasound transducer 16, thereby reducing rigidity. Helical flex circuits are described, for example, in PCT Patent Application Publication No. WO 02/07601, which published Jan. 31, 2002, and which is hereby incorporated by reference herein in its entirety. The helical flex circuit wrapping arrangement of FIG. 5 is, however, merely illustrative. Any suitable wrapping arrangement may be used to form the transducer array if desired.

Figure 6:
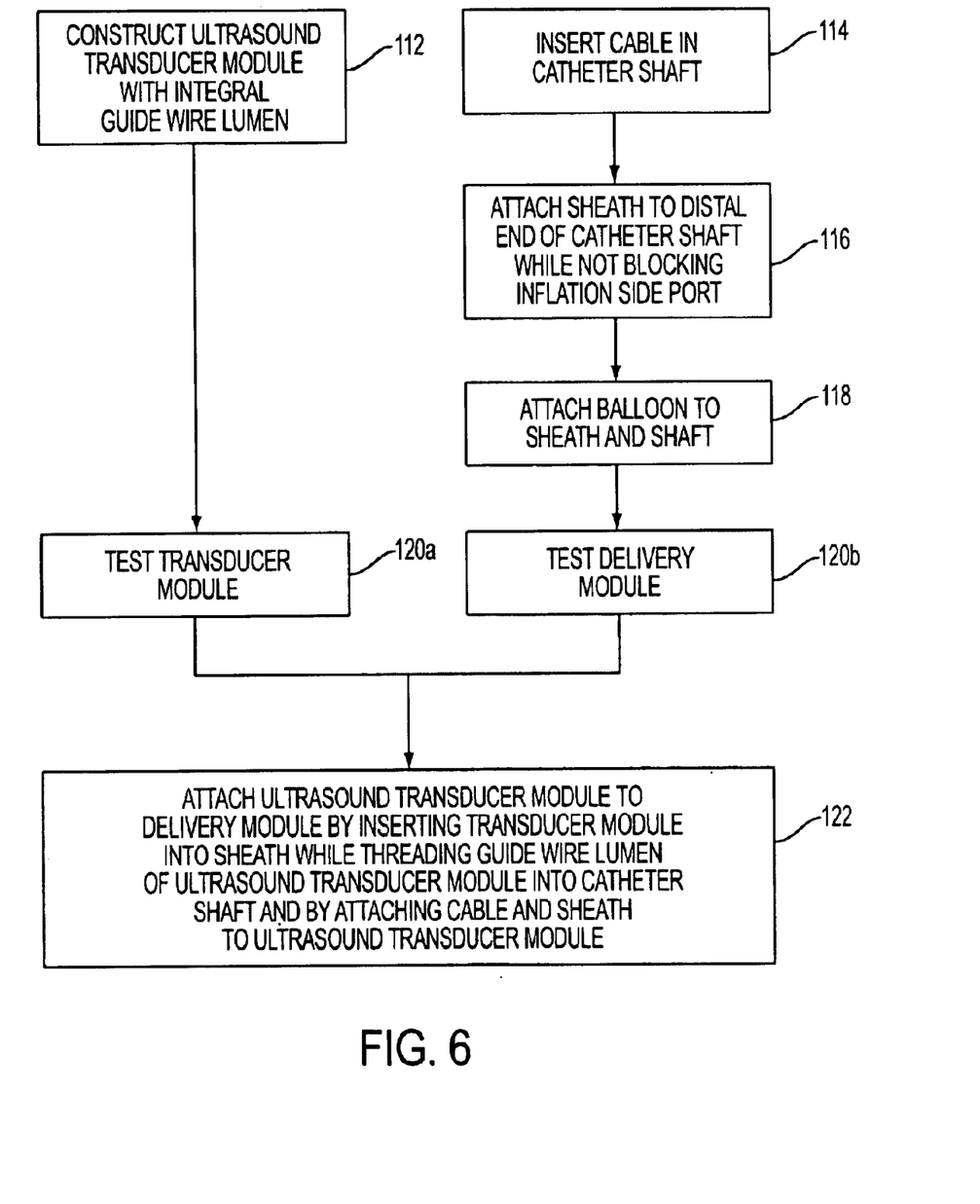
FIG. 6 is a flow chart of illustrative steps involved in fabricating an ultrasound catheter with a balloon using a modular assembly approach in accordance with the present invention.
Figures 7A, 7B, 7C:
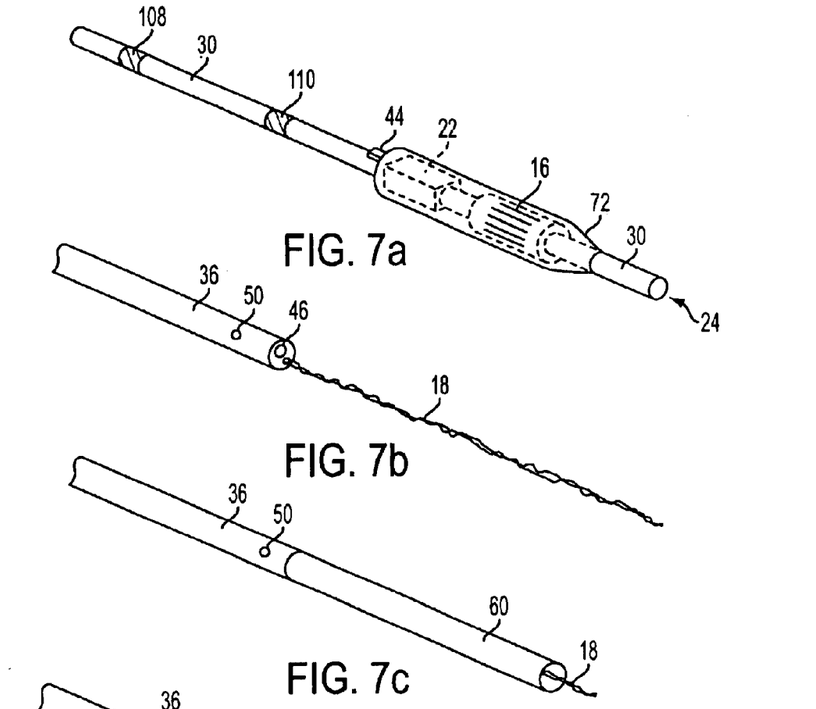
FIG. 7a is a perspective view of an illustrative ultrasound transducer module with an integral guide wire lumen that may be used in forming a catheter in accordance with the present invention.
FIG. 7b is a perspective view of an illustrative catheter shaft with a protruding electrical cable prior to attachment to the ultrasound transducer module in FIG. 7a in accordance with the present invention.
FIG. 7c is a perspective view showing how the catheter shaft of FIG. 7b may be provided with a sheath in accordance with the present invention.

Illustrative steps involved in using a modular approach for fabricating a catheter 10 having a distal ultrasound transducer and an expandable balloon are shown in FIG. 6. At step 112, an ultrasound transducer module may be constructed. For example, a flex circuit may be wrapped around a suitable support structure. The support structure may have a relatively short core tube that is attached to a longer piece of guide wire tubing or may be formed from a relatively longer section of guide wire tubing. An illustrative assembled ultrasound module is shown in FIG. 7a.

At step 114 of FIG. 6, the cable 18 may be inserted into catheter shaft 36. Shaft 36 may, if desired, be formed by coextruding a plastic shaft and an optional support wire, such as support member 38 (see FIG. 1). Integral lumens may be formed in shaft 36. For example, an inflation lumen 48 and a corresponding side port 50 may be formed, a lumen for cable 18 may be formed, and a portion of a guide wire lumen may be formed. The cable 18 may be inserted directly into a lumen in the shaft or may be placed in tubing (e.g., a length of hypotube) that is then inserted into a lumen in shaft 36. An illustrative shaft 36 in which wires 18 have been inserted is shown in FIG. 7b.

At step 116 of FIG. 6, sheath 60 may be attached to the shaft 36 (e.g., using adhesive or heat welding), preferably distal of side port 50. Sheath 60 may be, for example, a hollow plastic tube. A perspective view of the partially assembled catheter delivery module after sheath 60 has been added to shaft 36 is shown in FIG. 7c.

Figure 7D:
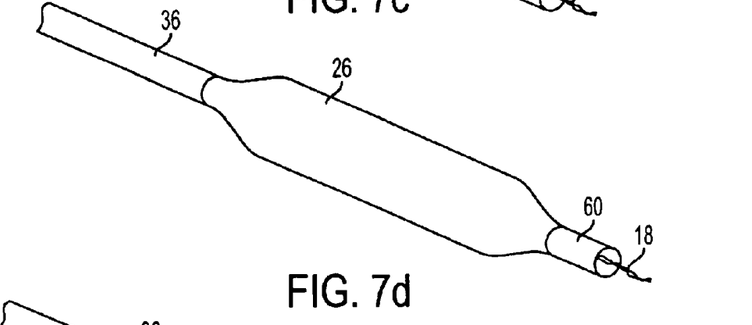
FIG. 7d is a perspective view showing how a balloon may be attached to the catheter assembly of FIG. 7c to form a delivery module during the catheter fabrication process in accordance with the present invention.

At step 118 of FIG. 6, balloon 26 may be distally attached to sheath 60, and proximally attached to shaft 36 proximal of side port 50, to form a substantially completed delivery module. Heat welding or adhesive attachment or other suitable attachment techniques may be used to attach these (and other) parts when forming catheter 10. After the balloon 26 has been attached to sheath 60, the assembled catheter module or assembly (which may be referred to as a delivery module because it is the portion of the catheter used to deliver the transducer and balloon to the desired location in the patient) appears as shown in FIG. 7d.

The two modules that combine to form catheter 10 may be individually tested. For example, the ultrasound transducer module may be tested at step 120a of FIG. 6, and the delivery module may be tested at step 120b. Testing may include, for example, strength testing, electrical testing (e.g., to ensure that the transducer is functioning properly), size testing, leak testing, etc. Testing each part of the catheter 10 separately may help to eliminate faulty parts (e.g., faulty transducers) before efforts are made to form the final catheter. Testing in this way may therefore help to enhance the yield of the catheter fabrication process. If desired, only the transducer modules or only the delivery modules (or neither) may be tested.

Figure 7E:
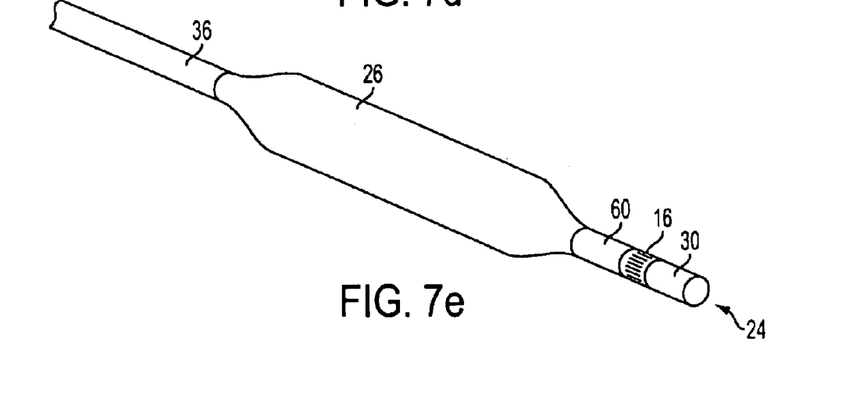
FIG. 7e is a perspective view showing the catheter following final assembly and attachment of the ultrasound transducer module and delivery module to each other in accordance with the present invention.

At step 122 of FIG. 6, the two parts of the catheter 10 (i.e., the delivery module and the transducer module) may be attached to each other. In particular, the proximal portion of guide wire lumen 30 of FIG. 7a may be inserted through the interior of sheath 60, through guide wire lumen exit port 46, through the guide wire lumen portion of shaft 36, and, if desired, through the remainder of shaft 36 and out of exit port 32 or 34. The cable wires 18 may be attached to the transducer at tab 44 and adhesive may be used to secure the two portions of the catheter together. The final assembled catheter may appear as shown in FIG. 7e.

Figure 8:
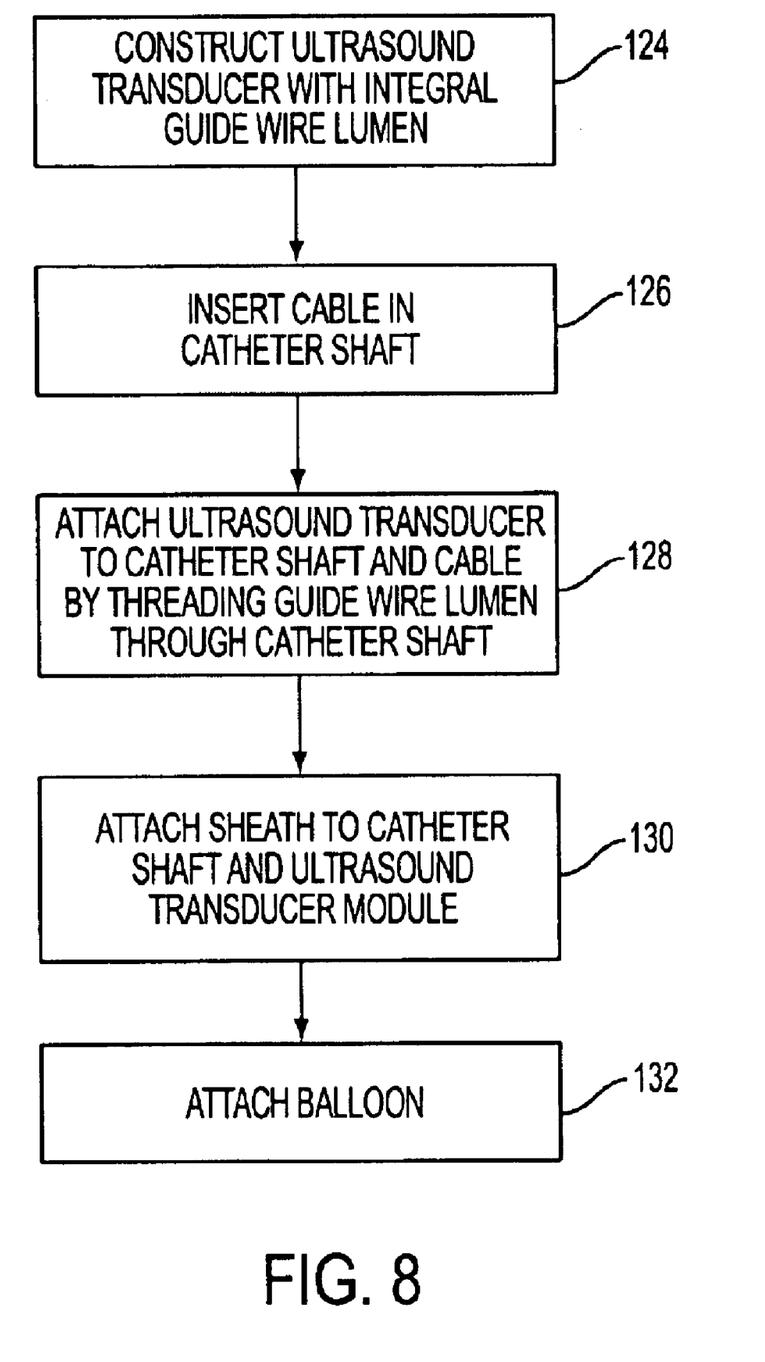
FIG. 8 is a flow chart of illustrative steps involved in fabricating an ultrasound catheter with a balloon using a non-modular assembly approach in accordance with the present invention.
Figures 9A, 9B, 9C, 9D:
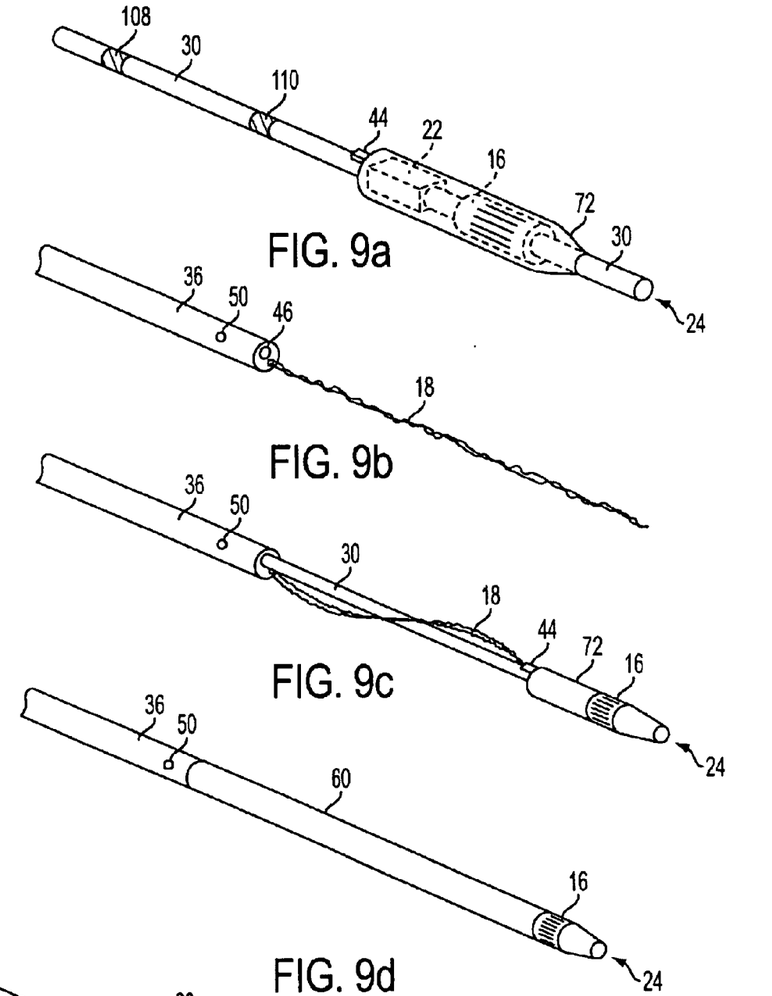
FIG. 9a is a perspective view of an illustrative ultrasound transducer and guide wire lumen that may be used in forming the catheter in accordance with the present invention.
FIG. 9b is a perspective view of an illustrative catheter shaft with a protruding electrical cable prior to attachment of the ultrasound transducer and guide wire lumen in accordance with the present invention.
FIG. 9c is a perspective view showing how the catheter shaft of FIG. 9b and ultrasound transducer and guide wire lumen of FIG. 9a may be joined in accordance with the present invention.
FIG. 9d is a perspective view showing how a sheath may be attached to the catheter assembly of FIG. 9c during the catheter fabrication process in accordance with the present invention.

Illustrative steps involved in using a non-modular approach for fabricating a catheter 10 having a distal ultrasound transducer and an expandable balloon are shown in FIG. 8. At step 124, an ultrasound transducer assembly with an integral guide wire lumen may be constructed. For example, a flex circuit may be wrapped around a suitable support structure. The support structure may have a relatively short core tube that is attached to a longer piece of guide wire tubing or may be formed from a relatively longer section of guide wire tubing. An illustrative assembled ultrasound transducer with an integral guide wire lumen is shown in FIG. 9a. The assembly may be provided with radiopaque markers 108 and 110.

At step 126 of FIG. 8, cable 18 may be inserted into catheter shaft 36. Shaft 36 may, if desired, be formed by coextruding a plastic shaft and an optional support wire, such as support member 38 (see FIG. 1). Integral lumens may be formed in shaft 36. For example, an inflation lumen 48 and a corresponding side port 50 may be formed, a lumen for cable 18 may be formed, and a portion of a guide wire lumen may be formed. The cable 18 may be inserted directly into the lumen in the shaft or may be placed in tubing (e.g., a length of hypotube) that is then inserted into the lumen in shaft 36. An illustrative shaft 36 in which electrical wires 18 have been inserted is shown in FIG. 9b.

At step 128 of FIG. 8, the ultrasound transducer (and accompanying guide wire lumen portion) may be attached to the catheter shaft 36 as shown in FIG. 9c. During step 128, the electrical wires of cable 18 may be connected to tab 44 of flex circuit 72. The guide wire lumen 30 may be threaded through the hole 46 in the end of shaft 36. If desired, the guide wire lumen 30 may be pulled through the entire shaft 36 until the guide wire lumen 30 exits shaft 36 at a more proximal location on shaft 36 (e.g., at rapid exchange exit port 32 or over-the-wire exit port 34 of FIG. 1). After the transducer, guide wire, and shaft have been assembled, the partially-assembled catheter may appear as shown in FIG. 9c.

At step 130 of FIG. 8, sheath 60 may be proximally attached to the shaft 36 distal of inflation side port 50, and may be distally attached to flex circuit 72 (e.g., using adhesive or heat welding). Sheath 60 may be, for example, a hollow plastic tube or a length of heat-shrinkable ("heat-shrink") tubing. An advantage of using heat-shrink tubing for sheath 60 is that heat may be applied to the heat-shrink tubing during step 130 to shrink the tubing and thereby reduce the diameter of the sheath 60 and the interior portions of the catheter (e.g., wires 18 and guide wire lumen 30) that are being shielded by the sheath. It is appropriate to use heat-shrink tubing during the assembly process of FIG. 8, because the heat-shrink tubing may be easily slid over the outer diameter of the assembled components of FIG. 9c and then heat shrunk into place. A perspective view of the partially assembled catheter after sheath 60 has been added is shown in FIG. 9d.

Figure 9E:
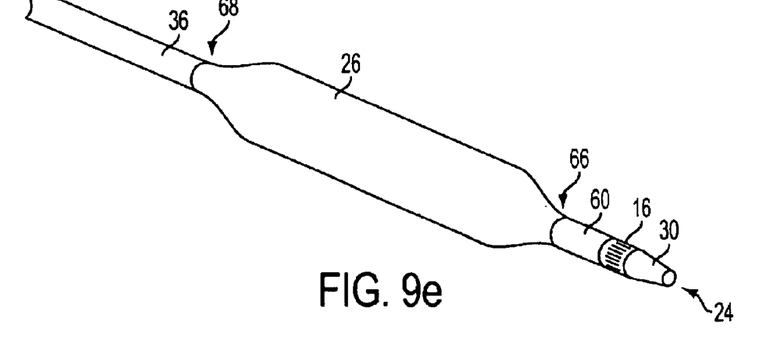
FIG. 9e is a perspective view showing the catheter following balloon attachment in accordance with the present invention.

At step 132 of FIG. 8, balloon 26 may be proximally attached to shaft 36 proximal of side port 50 (at proximal connection ring 68), and may be distally attached (at distal connection ring 66) to the outer portion of the flex circuit 72 that has been wrapped about the guide wire lumen 30 to form the transducer. Heat welding or adhesive or other suitable attachment techniques may be used to attach these (and other) parts when forming catheter 10. After the balloon 26 has been attached to sheath 60, the assembled catheter appears as shown in FIG. 9e.

It will be understood that the foregoing is merely illustrative of the principles of this invention, and that various modifications can be made by those skilled in the art without departing from the scope and spirit of the invention.

The invention claimed is:

1. A catheter that is guided over a guide wire in the body lumen of a patient during a medical procedure and that uses inflation fluid to deploy a balloon, comprising:

a proximal catheter portion and a distal catheter portion, wherein the distal catheter portion has a distal tip and a guide wire lumen that receives the guide wire and allows the catheter to be advanced over the guide wire;

an inflatable balloon on the distal catheter portion that receives the inflation fluid in its interior and that surrounds the guide wire lumen;

an ultrasound transducer on the distal catheter portion between the inflatable balloon and the distal tip;

electrical wires that extend from the proximal catheter portion through the balloon to the ultrasound transducer; and a sheath that extends through the balloon and isolates the electrical wires and the guide wire lumen from the inflation fluid.

2. The catheter defined in claim 1 wherein the sheath comprises heat-shrink tubing.

3. The catheter defined in claim 1 wherein the sheath comprises nonshrinkable tubing.

4. The catheter defined in claim 1 wherein the proximal catheter portion further comprises a rapid-exchange guide wire lumen exit port located proximal of the balloon.

5. The catheter defined in claim 1 wherein the proximal catheter portion has a proximal end and wherein the proximal catheter portion further comprises an over-the-wire guide wire lumen exit port located at the proximal end of the proximal catheter portion.

6. The catheter defined in claim 1 wherein the proximal catheter portion comprises a catheter shaft with an inflation fluid lumen and an inflation fluid port that communicates with the interior of the balloon.

7. The catheter defined in claim 1 wherein the proximal catheter portion comprises:

a catheter shaft; and a stiffening member that runs along the catheter shaft.

8. The catheter defined in claim 1 wherein the proximal catheter portion comprises:

a catheter shaft having a wire lumen through which the electrical wires run; and a length of hypotube surrounding at least some of the electrical wires in at least part of the wire lumen in the shaft.

9. The catheter defined in claim 1 wherein the proximal catheter portion comprises a catheter shaft having, for at least part of its length:

a wire lumen through which the electrical wires run;

an inflation fluid lumen and an inflation fluid port that communicates with the interior of the balloon; and a guide wire lumen that receives the guide wire.

10. The catheter defined in claim 1 wherein the ultrasound transducer comprises a flex circuit.

11. The catheter defined in claim 1 wherein the ultrasound transducer comprises a flex circuit and wherein the sheath is connected to the flex circuit.

12. A non-modular method for manufacturing a catheter, comprising:

constructing an ultrasound transducer assembly having a guide wire lumen;

providing a catheter shaft having electrical wires extending from its end;

attaching the ultrasound transducer assembly to the catheter shaft from which the electrical wires extend by attaching the guide wire lumen of the ultrasound assembly to the shaft and by attaching the electrical wires to the ultrasound transducer, so that a portion of the guide wire lumen and the electrical wires extend from the end of the catheter shaft to the ultrasound transducer after the ultrasound transducer assembly has been attached to the catheter shaft;

covering the portion of the guide wire lumen and electrical wires with a sheath; and attaching a balloon over the sheath at a proximal end of the ultrasound transducer, such that the sheath isolates inflation fluid in the interior of the balloon from the portion of the guide wire lumen and the electrical wires.

13. The method defined in claim 12 wherein covering the portion of the guide wire lumen and electrical wires with the sheath comprises using heat to shrink a length of heat-shrink tubing over the guide wire lumen and electrical wires.

14. The method defined in claim 12 further comprising forming a side port in the catheter shaft that is used to introduce the inflation fluid into the interior of the balloon.

15. The method defined in claim 12 further comprising encasing at least some of the electrical wires in a hypotube inside at least part of the catheter shaft.

16. The method defined in claim 12 further comprising forming the ultrasound transducer assembly from a flex circuit wrapped around the integral guide wire lumen.

17. A modular method for manufacturing a catheter, comprising:

constructing an ultrasound transducer module having a guide wire lumen;

constructing a delivery module by:

providing a catheter shaft having electrical wires extending from its distal end and having an inflation port for dispensing inflation fluid;

attaching a sheath to the distal end of the catheter shaft while not blocking the inflation port; and attaching a balloon to the shaft and to the sheath that has been attached to the shaft, wherein the balloon receives the inflation fluid in its interior through the inflation port; and attaching the ultrasound transducer module to the delivery module.

18. The method defined in claim 17 further comprising testing the ultrasound transducer module before attaching the ultrasound transducer module to the delivery module.

19. The method defined in claim 17 further comprising forming the inflation port in a side of the catheter shaft to introduce inflation fluid into the interior of the balloon.

20. The method defined in claim 17 further comprising constructing the ultrasound transducer by wrapping a flex circuit around a support lumen in a helix.

21. The method defined in claim 17 wherein attaching the sheath further comprises passing the electrical wires through the sheath.

22. The method defined in claim 17 wherein attaching the ultrasound transducer module further comprises:

threading the guide wire lumen through the sheath into the catheter shaft; and electrically coupling the electrical wires to the ultrasound transducer module.

* * * * *